United States Patent
Bowditch et al.

(10) Patent No.: US 8,925,546 B2
(45) Date of Patent: *Jan. 6, 2015

(54) POSITIVE AIRWAY PRESSURE SYSTEM WITH HEAD POSITION CONTROL

(71) Applicant: Hancock Medical, Inc., Mountain View, CA (US)

(72) Inventors: Nathaniel L. Bowditch, Menlo Park, CA (US); Thomas G. Goff, Mountain View, CA (US); Tarmigan Casebolt, San Francisco, CA (US)

(73) Assignee: Hancock Medical, Inc., Mountain View, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 13/667,795

(22) Filed: Nov. 2, 2012

(65) Prior Publication Data

US 2013/0056004 A1 Mar. 7, 2013

Related U.S. Application Data

(63) Continuation of application No. 13/244,834, filed on Sep. 26, 2011, now Pat. No. 8,327,846.

(60) Provisional application No. 61/440,685, filed on Feb. 8, 2011.

(51) Int. Cl.
*A61M 16/00* (2006.01)
*A61M 16/06* (2006.01)
*A61M 16/08* (2006.01)

(52) U.S. Cl.
CPC ............ *A61M 16/0051* (2013.01); *A61M 16/00* (2013.01); *A61M 16/0683* (2013.01); *A61M 16/0069* (2013.01); *A61M 16/0057* (2013.01); *A61M 16/0875* (2013.01); *A61M 2205/70* (2013.01); *A61M 2205/8206* (2013.01); *A61M 2205/8262* (2013.01); *A61M 2209/088* (2013.01); *A61M 2210/06* (2013.01); *A61M 2230/62* (2013.01); *A61M 2230/63* (2013.01)
USPC ............ 128/204.23; 128/204.18; 128/204.21; 128/205.23

(58) Field of Classification Search
USPC ............ 128/200.24, 201.22, 201.23, 201.24, 128/204.18, 204.21, 204.23, 204.26, 128/205.25, 206.21, 206.28, 207.11, 207.13
See application file for complete search history.

(56) References Cited

U.S. PATENT DOCUMENTS

| | | | |
|---|---|---|---|
| 3,649,964 | A | 3/1972 | Schoelz et al. |
| 3,721,233 | A | 3/1973 | Montgomery et al. |

(Continued)

FOREIGN PATENT DOCUMENTS

| | | |
|---|---|---|
| FR | 2853838 A1 | 10/2004 |
| WO | WO91/19527 A1 | 12/1991 |

(Continued)

OTHER PUBLICATIONS

Cartwright; Effect of sleep position on sleep apnea severity; Sleep; 7(2); pp. 110-114; 1984 (year of pub. sufficiently earlier than effective US filing date and any foreign priority date).

(Continued)

*Primary Examiner* — Justine Yu
*Assistant Examiner* — LaToya M Louis
(74) *Attorney, Agent, or Firm* — Shay Glenn LLP

(57) ABSTRACT

The invention is directed to a positive airway pressure (PAP) system with a head mounted harness assembly with a housing and a head position sensor located within or secured to the housing that detects the position of a patient's head, and communicates this head position information to a controller of the system which may be disposed within the housing having the position sensor or a second housing. The controller varies the output pressure of the pressure source, e.g. a rotary compressor, based, at least in part, on the head position information provided by the head position sensor. In a preferred embodiment, the position sensor is an accelerometer.

8 Claims, 17 Drawing Sheets

(56) References Cited

U.S. PATENT DOCUMENTS

| | | |
|---|---|---|
| 3,736,927 A | 6/1973 | Misaqi |
| 3,822,698 A | 7/1974 | Guy |
| 3,881,198 A | 5/1975 | Waters |
| 3,998,213 A | 12/1976 | Price |
| 4,019,508 A | 4/1977 | Der Estephanian et al. |
| 4,233,972 A | 11/1980 | Hauff et al. |
| 4,297,999 A | 11/1981 | Kitrell |
| 4,381,267 A | 4/1983 | Jackson |
| 4,430,995 A | 2/1984 | Hilton |
| 4,549,542 A | 10/1985 | Chien |
| 4,590,951 A | 5/1986 | O'Connor |
| 4,644,947 A | 2/1987 | Whitwam et al. |
| 4,765,316 A | 8/1988 | Marshall |
| 4,782,832 A | 11/1988 | Trimble et al. |
| 4,802,485 A | 2/1989 | Bowers et al. |
| 4,829,998 A | 5/1989 | Jackson |
| 4,836,219 A | 6/1989 | Hobson et al. |
| 4,944,310 A | 7/1990 | Sullivan |
| 5,035,239 A | 7/1991 | Edwards |
| 5,046,492 A | 9/1991 | Stackhouse et al. |
| 5,054,480 A | 10/1991 | Bare et al. |
| 5,054,484 A | 10/1991 | Hebeler |
| 5,104,430 A | 4/1992 | Her Mou |
| 5,113,853 A | 5/1992 | Dickey |
| 5,154,168 A | 10/1992 | Schlobohm |
| 5,303,701 A | 4/1994 | Heins et al. |
| 5,318,020 A | 6/1994 | Schegerin |
| 5,349,946 A | 9/1994 | Mccomb |
| 5,353,788 A | 10/1994 | Miles |
| 5,372,130 A | 12/1994 | Stern et al. |
| 5,394,870 A | 3/1995 | Johansson |
| 5,461,934 A | 10/1995 | Budd |
| 5,485,851 A | 1/1996 | Erickson |
| 5,517,986 A | 5/1996 | Starr et al. |
| 5,533,500 A | 7/1996 | Her Mou |
| RE35,339 E | 10/1996 | Rapoport |
| 5,564,124 A | 10/1996 | Elsherif et al. |
| 5,577,496 A | 11/1996 | Blackwood et al. |
| 5,649,533 A | 7/1997 | Oren |
| 5,657,752 A | 8/1997 | Landis et al. |
| 5,769,071 A | 6/1998 | Turnbull |
| 5,928,189 A | 7/1999 | Phillips et al. |
| 5,937,855 A | 8/1999 | Zdrojkowski et al. |
| 5,950,621 A | 9/1999 | Klockseth et al. |
| 5,954,050 A | 9/1999 | Christopher |
| 5,961,447 A | 10/1999 | Raviv et al. |
| 6,050,262 A | 4/2000 | Jay |
| 6,122,773 A | 9/2000 | Katz |
| 6,135,106 A | 10/2000 | Dirks et al. |
| 6,179,586 B1 | 1/2001 | Herb et al. |
| 6,213,119 B1 | 4/2001 | Brydon et al. |
| 6,349,724 B1 | 2/2002 | Burton et al. |
| 6,367,474 B1 | 4/2002 | Berthon Jones et al. |
| 6,371,112 B1 | 4/2002 | Bibi |
| 6,393,617 B1 | 5/2002 | Paris et al. |
| 6,397,845 B1 | 6/2002 | Burton |
| 6,431,171 B1 | 8/2002 | Burton |
| 6,435,180 B1 | 8/2002 | Hewson et al. |
| 6,435,184 B1 | 8/2002 | Ho |
| 6,513,526 B2 | 2/2003 | Kwok et al. |
| 6,532,960 B1 | 3/2003 | Yurko |
| 6,561,190 B1 | 5/2003 | Kwok |
| 6,561,191 B1 | 5/2003 | Kwok |
| 6,615,831 B1 | 9/2003 | Tuitt et al. |
| 6,622,311 B2 | 9/2003 | Diaz et al. |
| 6,634,864 B1 | 10/2003 | Young et al. |
| 6,694,978 B1 | 2/2004 | Bennarsten |
| 6,705,314 B1 | 3/2004 | O'Dea |
| 6,709,405 B2 | 3/2004 | Jonson |
| 6,752,146 B1 | 6/2004 | Altshuler et al. |
| 6,772,760 B2 | 8/2004 | Frater et al. |
| 6,772,762 B2 | 8/2004 | Piesinger |
| 6,793,629 B2 | 9/2004 | Rapoport et al. |
| 6,854,465 B2 | 2/2005 | Bordewick et al. |
| 6,881,192 B1 | 4/2005 | Park |
| 6,889,691 B2 | 5/2005 | Eklund et al. |
| 6,895,959 B2 | 5/2005 | Lukas |
| 6,895,962 B2 | 5/2005 | Kullik et al. |
| 6,920,877 B2 | 7/2005 | Remmers et al. |
| 6,932,084 B2 | 8/2005 | Estes et al. |
| 6,973,929 B2 | 12/2005 | Gunaratnam |
| 6,990,980 B2 | 1/2006 | Richey |
| 7,019,652 B2 | 3/2006 | Richardson |
| 7,069,932 B2 | 7/2006 | Eaton et al. |
| 7,089,941 B2 | 8/2006 | Bordewick et al. |
| 7,096,864 B1 | 8/2006 | Mayer et al. |
| 7,118,608 B2 | 10/2006 | Lovell |
| 7,156,090 B2 | 1/2007 | Nomori |
| 7,178,525 B2 | 2/2007 | Matula et al. |
| 7,195,014 B2 | 3/2007 | Hoffman |
| 7,200,873 B2 | 4/2007 | Klotz et al. |
| 7,204,250 B1 | 4/2007 | Burton |
| 7,255,103 B2 | 8/2007 | Bassin |
| 7,357,136 B2 | 4/2008 | Ho et al. |
| 7,406,996 B2 | 8/2008 | Schuh |
| 7,471,290 B2 | 12/2008 | Wang et al. |
| 7,487,778 B2 | 2/2009 | Freitag |
| 7,516,743 B2 | 4/2009 | Hoffman |
| 7,575,005 B2 | 8/2009 | Mumford et al. |
| 7,588,033 B2 | 9/2009 | Wondka |
| 7,664,546 B2 | 2/2010 | Hartley et al. |
| 7,681,575 B2 | 3/2010 | Wixey et al. |
| 7,766,841 B2 | 8/2010 | Yamamoto et al. |
| 7,913,692 B2 | 3/2011 | Kwok |
| 7,934,500 B2 | 5/2011 | Madaus et al. |
| 7,942,824 B1 | 5/2011 | Kayyali et al. |
| 8,020,557 B2 | 9/2011 | Bordewick et al. |
| 8,061,354 B2 | 11/2011 | Schneider et al. |
| 8,172,766 B1 | 5/2012 | Kayyali et al. |
| 8,327,846 B2 | 12/2012 | Bowditch et al. |
| 8,336,546 B2 | 12/2012 | Bowditch et al. |
| 8,353,290 B2 | 1/2013 | Adams |
| 8,453,640 B2 | 6/2013 | Martin et al. |
| 8,475,370 B2 | 7/2013 | McCombie et al. |
| 8,517,017 B2 | 8/2013 | Bowditch et al. |
| 2002/0078958 A1 | 6/2002 | Stenzler |
| 2002/0104541 A1 | 8/2002 | Bibi et al. |
| 2003/0062045 A1 | 4/2003 | Woodring et al. |
| 2003/0079749 A1 | 5/2003 | Strickland et al. |
| 2004/0079373 A1 | 4/2004 | Mukaiyama et al. |
| 2004/0163648 A1 | 8/2004 | Burton |
| 2004/0186681 A1 | 9/2004 | Harle |
| 2004/0226562 A1 | 11/2004 | Bordewick |
| 2005/0005937 A1 | 1/2005 | Farrugia et al. |
| 2005/0034724 A1 | 2/2005 | O'Dea |
| 2005/0068639 A1 | 3/2005 | Pierrat et al. |
| 2005/0131288 A1 | 6/2005 | Turner et al. |
| 2005/0133039 A1 | 6/2005 | Wood |
| 2005/0188991 A1 | 9/2005 | Sun et al. |
| 2006/0037613 A1 | 2/2006 | Kwok et al. |
| 2006/0081250 A1 | 4/2006 | Bordewick et al. |
| 2006/0096596 A1 | 5/2006 | Occhialini et al. |
| 2006/0150973 A1 | 7/2006 | Chalvignac |
| 2006/0150978 A1 | 7/2006 | Doshi et al. |
| 2006/0180149 A1 | 8/2006 | Matarasso |
| 2006/0231097 A1 | 10/2006 | Dougherty et al. |
| 2007/0000493 A1 | 1/2007 | Cox |
| 2007/0113854 A1 | 5/2007 | Mcauliffe |
| 2007/0208269 A1 | 9/2007 | Mumford et al. |
| 2007/0240716 A1 | 10/2007 | Marx |
| 2007/0247009 A1 | 10/2007 | Hoffman et al. |
| 2007/0251527 A1 | 11/2007 | Sleeper |
| 2007/0277825 A1 | 12/2007 | Bordewick et al. |
| 2008/0006275 A1 | 1/2008 | Nickelson et al. |
| 2008/0053451 A1 | 3/2008 | Bordewick et al. |
| 2008/0127976 A1 | 6/2008 | Acker et al. |
| 2008/0178879 A1 | 7/2008 | Roberts et al. |
| 2008/0185002 A1 | 8/2008 | Berthon-Jones et al. |
| 2008/0216831 A1 | 9/2008 | McGinnis et al. |
| 2008/0304986 A1 | 12/2008 | Kenyon et al. |
| 2009/0044810 A1 | 2/2009 | Kwok et al. |
| 2009/0065005 A1 | 3/2009 | Ades |
| 2009/0078255 A1 | 3/2009 | Bowman et al. |
| 2009/0078258 A1 | 3/2009 | Bowman et al. |

(56) References Cited

U.S. PATENT DOCUMENTS

| | | |
|---|---|---|
| 2009/0194101 A1 | 8/2009 | Kenyon et al. |
| 2010/0024811 A1 | 2/2010 | Henry et al. |
| 2010/0180895 A1 | 7/2010 | Kwok et al. |
| 2010/0191076 A1 | 7/2010 | Lewicke et al. |
| 2010/0240982 A1 | 9/2010 | Westbrook et al. |
| 2010/0312513 A1 | 12/2010 | Mayor et al. |
| 2011/0056489 A1 | 3/2011 | Slaker et al. |
| 2011/0100366 A1 | 5/2011 | Chou |
| 2011/0105915 A1 | 5/2011 | Bauer et al. |
| 2011/0192400 A9 | 8/2011 | Burton et al. |
| 2011/0295083 A1 | 12/2011 | Doelling et al. |
| 2012/0152239 A1 | 6/2012 | Shikani et al. |
| 2012/0152255 A1 | 6/2012 | Barlow et al. |
| 2012/0266873 A1 | 10/2012 | Lalonde |
| 2012/0298099 A1 | 11/2012 | Lalonde |
| 2012/0304985 A1 | 12/2012 | Lalonde |
| 2013/0104883 A1 | 5/2013 | Lalonde |
| 2013/0146054 A1 | 6/2013 | Ho |
| 2013/0306074 A1 | 11/2013 | Bowditch et al. |
| 2014/0076319 A1 | 3/2014 | Bowditch et al. |
| 2014/0144445 A1 | 5/2014 | Bowditch et al. |

FOREIGN PATENT DOCUMENTS

| | | |
|---|---|---|
| WO | WO99/13931 A1 | 3/1999 |
| WO | WO99/21602 A1 | 5/1999 |
| WO | WO02/085417 A2 | 10/2002 |
| WO | WO2007/149446 A2 | 12/2007 |
| WO | WO2008/028247 A1 | 3/2008 |
| WO | WO2011/127385 A1 | 10/2011 |

OTHER PUBLICATIONS

Colrain et al.; The use of a nasal resistance valve to treat sleep disordered breathing (Abstract No. 0518); Sleep 2008 22nd Ann. Mtg. Assoc. Prof. Sleep Soc., LLC; Baltimore, MD; vol. 31, Abstract Suppl.; p. A172; Jun. 7-12, 2008.

Gunaratnam et al.; U.S. Appl. No. 60/494,119 entitled "Nasal Assembly," filed Aug. 12, 2003 (119 pgs.).

Høfsoy et al.; Monitoring and therapy of sleep related breathing disorders; IEEE; 6th Ann. Workshop on Wearable Micro and Nano Technologies for Personalized Heath (pHealth); pp. 41-44; Jun. 24-26, 2009.

Kwok, Philip R.; U.S. Appl. No. 60/505,718 entitled "Ventilator mask and system," filed Sep. 25, 2003 (37 pgs.).

Massie et al.; Acceptance and adherence of a novel device in the treatment of mild to moderate obstructive sleep apnea (Abstract No. 0644); Sleep 2008 22nd Ann. Mtg. Assoc. Prof. Sleep Soc., LLC; Baltimore, MD; vol. 31, Abstract Suppl.; p. A211; Jun. 7-12, 2008.

Oksenberg et al.; Association of body position with severity of apneic events in patients with severe non-positional obstructive sleep apnea; Chest; 118(4); pp. 1018-1024; Oct. 2000.

Penzel et al.; Effect of sleep position and sleep stage on the collapsibility of the upper airways in patients with sleep apnea; Sleep; 24(1); pp. 90-95; Feb. 2001.

Pevernagie et al.; Relations between sleep stage, posture and effective nasal CPAP levels in OSA; Sleep; 15(2); pp. 162-167; 1992 (year of pub. sufficiently earlier than effective US filing date and any foreign priority date).

Rosenthal et al.; A novel expiratory pressure device to treat mild-moderate OSA (Abstract No. 0634); Sleep 2008 22nd Ann. Mtg. Assoc. Prof. Sleep Soc., LLC; Baltimore, MD; vol. 31, Abstract Suppl.; p. A208; Jun. 7-12, 2008.

POSITIVE AIRWAY PRESSURE SYSTEM WITH HEAD POSITION CONTROL

RELATED APPLICATIONS

This application is a continuation of U.S. patent application Ser. No. 13/244,834, filed on Sep. 26, 2011, now U.S. Pat. No. 8,327,846, which is related to and claims priority to provisional application Ser. No. 61/440,685, filed Feb. 8, 2011, the disclosure of each of which is incorporated herein by reference in its entirety.

FIELD OF THE INVENTION

The invention is generally directed to a system and method for controlling the treatment a patient receives and particularly to controlling a Positive Airway Pressure (PAP) device.

BACKGROUND OF THE INVENTION

During sleep, all muscles, including those of the upper airway, lose tone and relax. Obstructive Sleep Apnea (OSA) occurs when tissue blocks the upper airway during sleep. This will cause a drop in blood oxygen and a rise in blood carbon dioxide. The brain will sense these changes, and awaken the person enough to restore muscle tone to the structures of the upper airway, and the airway will reopen.

The severity of OSA is determined by the number of blockages per hour of sleep, also called the apnea-hypopnea index (AHI). These include complete blockages (apneas) and partial blockages (hypopneas). The severity of OSA, as determined by a sleep study, is classified as follows:

| SEVERITY | BLOCKAGES PER HOUR |
| --- | --- |
| Mild | 5-15 |
| Moderate | 15-30 |
| Severe | 30+ |

OSA disrupts restorative sleep. Chronic fatigue has long been recognized as the hallmark of OSA. But more recently, large clinical studies have shown a strong link between OSA and stroke and death. This link is independent of other risk factors for cardiovascular disease such as hypertension, obesity, high cholesterol, smoking and diabetes.

As discussed above, several structures can cause blockage of the upper airway: the tongue, the soft palate, the uvula, the lateral walls of the pharynx, the tonsils and the epiglottis. In most patients, the blockage is caused by a combination of these anatomical structures.

Many current procedures and devices have been used to stabilize, modify or remove tissue in the airway to treat OSA. In uvulopalatopharygoplasty (UPPP), the uvula, part of the soft palate and the tonsils are removed. A Repose stitch is used to tie the tongue to the mandible to prevent its posterior movement. Oral appliances move the mandible forward (very slightly) to create more space in the airway.

None of these approaches has achieved much more than a 50% success rate, with success defined as a 50% decrease in AHI to a score below 20. The limited success of these approaches likely stems from the fact that they don't address all anatomical sources of a blockage.

The most widely used therapeutic system for OSA is a PAP system such as a continuous positive airway pressure (CPAP) system. A CPAP system usually consists of three parts: a mask forming a largely airtight seal over the nose or nose and mouth, pressurizing housing or console and an elongated tube connecting the two. The mask contains one or more holes, usually at the junction with the tube. A CPAP system works by pressurizing the upper airway throughout the breathing cycle, essentially inflating the airway to keep it open. A CPAP system thus maintains a pneumatic splint throughout the respiratory cycle.

Unlike interventions that treat specific blockages, a CPAP system addresses all potential blockage sites. The success rate in patients (dropping AHI by >50%) exceeds 80%, and its cure rate (decreasing AHI below 5) is close to 50%. The drawback to a CPAP system is poor patient compliance, i.e. continuous use by the patient. In one large study, only 46% of patients were compliant with a CPAP system, even though compliance was defined as using the CPAP system at least 4 hours per night at least 5 nights per week.

Critical pressure is the airway pressure a given patient requires to maintain open airway during sleep. Critical pressure is measured in cm of water, and will typically be between 6 and 14 cm of water for a patient requiring CPAP. In a given patient, the efficacy of a CPAP system goes up as pressure is increased. But, as higher pressure makes the CPAP system more uncomfortable to the patient, patient compliance drops. The goal of the healthcare professional in setting up a CPAP system for a patient is to achieve critical pressure without exceeding it. This will make the CPAP system both effective and tolerable.

In a given patient, there are several factors which affect critical pressure. The pressure supplied by the CPAP system necessary to achieve critical pressure varies through the breathing cycle. When a patient is exhaling, the patient is supplying some air pressure to the airway, and thus requires limited pressure from the CPAP system to maintain critical pressure. But when the patient is inhaling, he is decreasing pressure in the airway. During inhalation, more pressure is required by the CPAP system to maintain critical pressure in the airway. There are now many available CPAP systems that monitor the respiratory cycle, and provide less pressure during the portions of the respiratory cycle when less external pressure is required to maintain critical pressure in the airway. Such adaptive systems, which include systems commercially known as BiPAP and C-Flex, make CPAP systems more comfortable, improving the compliance of many patients. So, during the respiratory cycle, critical pressure does not change. But the pressure contributed by the CPAP system to maintain critical pressure changes during the respiratory cycle.

Critical pressure can change based on sleeping position in many patients. Critical pressure will usually be higher when a patient is in a supine position (i.e. on his back) than when a patient is in a lateral position (on his side). This is because many of the structures that can block the airway, such as the tongue and uvula, are anterior to the airway. When a patient is in a supine position, gravity pulls these structures toward the airway, and a greater pressure (critical pressure) is required to keep the airway open. When a patient is in a lateral position, gravity is not pulling these structures directly into the airway, and thus less pressure is required to maintain an open airway. This was demonstrated in a study published in 2001 (Penzel T. et al. 2001. *Effect of Sleep Position and Sleep Stage on the Collapsibility of the Upper Airways in Patients with Sleep Apnea*; SLEEP 24(1): 90-95.). Additionally, most sleep studies used to diagnose OSA will track body position and will determine whether a patient has airway blockages more frequently when sleeping in a supine position. Other sleep studies have found that the lateral position results in fewer observed apneas than the supine position. (Cartwright R. et al.

1984 Effect of Sleep Position on Sleep Apnea Severity: SLEEP 7:110-114), (Pevernagie D. et al. 1992 Relations Between Sleep Stage, Posture, and Effective Nasal CPAP Levels in OSA: SLEEP 15: 162-167). Further studies have shown that apnea events in the supine position tend to be more sever, have, longer duration, be accompanied by a greater oxygen desaturation and increased heart rate, and be more likely to result in arousals and awakenings. (Oksenberg A. et al. 2000 Association of Body Position with Severity of Apneic Events in Patients with Severe Non-positional Obstructive Sleep Apnea: CHEST 118: 1018-1024)

SUMMARY OF THE INVENTION

This invention is directed to a positive airway pressure (PAP) system and method for treating of a patient with OSA or other breathing problems wherein the system has a head position sensor that is mounted onto the top of the patient's head and a pressure source that has an output pressure controlled by a head position signal from the head position sensor. The PAP system includes at least one housing having an interior configured to receive a system component and being configured to be secured to the top of the patient's head, preferably in a median position. One system component is a gas pressure source, such as a compressor, with a controllable output pressure which is disposed within the interior of the housing and preferably has a controllable motor drive. The gas pressure source has an outlet opening which is configured to be connected to a tubular member that preferably leads to a mask which is configured to sealingly fit over the patient's nose and/or mouth. The PAP system has a harness assembly which is configured to secure at least part of the system to the top a the patient's head.

A PAP system embodying features of the invention has a head position sensor, such as an accelerometer, that is secured within or to a system housing or on or to the harness assembly that is configured to secure at least part of the PAP system to the user's head. The head position sensor is configured to sense the position of the patient's head with respect to a reference plane (e.g. a horizontal plane) and to generate a signal representing the sensed position of the patient's head. A suitable accelerometer is a Freescale 3-Axis MEMS Accelerometer (MMA845XQ), particularly the MMA8453Q model, which generates a signal series representing a three axis orientation with respect to gravity.

Another system component is a controller, preferably a microprocessor such as Atmel AVR Model # ATMMega328, that is provided to control the PAP system so as to adjust the output of the gas pressure source according to the sensed position of the patient's head to provide a critical pressure to the patient's airway passage to maintain patency. The controller is preferably secured within the system's housing and is configured to receive the head position signals transmitted from the head position sensor. The controller is configured to receive the head position signals and to determine a suitable pressure source output pressure for the particular sensed head position from the received head position signal. The controller preferably has a stored relationship between sensed head position and suitable pressure source output pressure and is configured to generate a control signal for the pressure source representing the determined suitable gas pressure. The control signal generated by the controller is transmitted to the pressure source, e.g. the driving motor of a compressor, to control the output of the pressure source so as to provide the determined suitable gas pressure for the sensed position: of the patient's head.

In one embodiment, a pressure sensor senses the actual gas pressure directed to or received by the user and the controller compares the directed or received sensed pressure with the desired or determined suitable pressure and adjusts the control signal to the pressure source so as to provide the pressure source output that provides the critical pressure that maintains patency in the patient's airway passage.

Alternatively, the pressure source may be operated at a constant pressure level and a control valve disposed between the pressure source and the patient's mask receives the control signal to control the output pressure. The control valve may be provided in the compressor outlet, in a gas flow line to the patient's mask or in the patient's mask, to provide the determined suitable gas pressure to the patient that maintains patency in the patient's airway passage.

Although the accelerometer and the controller are described herein as two separate devices, they may be combined into a single device.

The controller is configured to determine suitable compressor output pressures from the head position signal-pressure source output pressure relationship for at least two patient head positions, one head position may be a supine position and another second patient position might be a lateral position, preferably at least 20° from the supine position. In one embodiment, the controller may be provided with a readable library listing a plurality of head position signals with corresponding suitable pressure source output pressures. In another embodiment, the controller has a preprogrammed algorithm representing a relationship between head position signal and corresponding suitable pressure source output pressure. The microprocessor is configured to use the received head position signals to calculate from the algorithm suitable pressure source output pressures and generate suitable control signals for the pressure source. The relationship between the head position signal and suitable pressure source output pressure may be a stepped function, e.g. two or more positions with suitable pressure source output pressure or a continuous function. There may be a gradual change in pressure between stepped functions. The continuous function preferably has a greater rate of change in the pressure source output pressure with respect to head position with head positions between about 30° and 60° from the supine position (0°).

The set point for a suitable pressure source output pressure for one of the head positions, e.g. the supine position, may be set by a health professional based upon the patient's sleep study. The set point for other position may also be set by the health professional.

In one embodiment, the supine position may be defined as within 30° of vertical, with vertical being the sleeping position where the nose is pointed directly upward, orthogonal to the sleeping plane which is horizontal.

The pressure source is preferably a rotary blower such as the Nidec Copal TF037C, which has a turbine and a controllable drive motor. An alternative pressure source may be a bellows system which maintains a pressurized storage tank that provides pressurized breathing gas to the patient's mask. Other gas pressure sources may be utilized.

The electrical power source for the pressure source drive motor is preferably a portable power source component such as one or more batteries which may be provided within the system housing. However, the electrical power source may be an electrical power cord for connection to an electrical source (e.g. a wall outlet or a separate battery pack) and may be provided to directly supply electrical power to the pressure source and/or to recharge one or more batteries. The electrical power source is connected to and powers the drive motor that controls the output pressure of the pressure source such as a rotary compressor.

In one embodiment, the system housing may be one or more separate housings; and is mounted on top of a patient's head, preferably in a medial position, by a one or more straps of the harness assembly that are secured to the housing. Other means to secure the system housing to the patient's head may be used.

Initially, a health professional may set the output pressure of the compressor for one or more of the patient's head positions that have been based upon a sleep study performed on the patient. The second head position should be at least 20° away from the first head position. Optionally, the health professional may also set the set point for the output pressure of the system when the patient's head is at other positions. Preferably, the controller is programmed to select a suitable compressor output pressure from a preset table or library for at least one head position or determine a suitable pressure from a preprogrammed algorithm that is based upon the sensed position of the patient's head. The algorithm defines the relationship between the head position signal and the suitable compressor output pressure.

With the PAP system mounted on the patient's head, the head position sensor is first calibrated, preferably when the patient's head is in a supine position. The calibrated head position sensor senses the patient's head position and generates a sensed head position signal which is transmitted to the controller. The controller determines a suitable pressure source output pressure for the sensed head position signal and generates a control signal for the pressure source to provide the suitable pressure output pressure. In one embodiment, the controller compares the determined suitable pressure source output pressure with the current pressure output of the pressure source and if they differ by a specified amount, the controller generates a new control signal for the pressure source. If they do not differ by the specified amount the system loops back and continues to monitor the patient's head position.

The pressure source output pressure requirements can vary between a low point at exhalation to a high point at inhalation for each position of the patient's head which forms an output pressure envelope for the patient.

During sleep, the position of the patient's head can be the most important determinant of critical pressure for the patient since the anatomical structures that might block the airway (such as the tongue, the soft palate, the uvula and the tonsils) are in the head. Thus, the position sensor that determines the position of the head can be valuable in effectively controlling the pressure output of a PAP system.

In one embodiment the PAP system provides a first (higher) gas pressure from the compressor when the patient's head is in a supine position and a second (lower) pressure when the patient's head is in a lateral position. The gas pressure supplied to the patient when the patient's head is in a lateral position would likely be 1-8 cm of water less than the pressure supplied when the patient's head is in the supine position. Additionally, the PAP system can vary pressure more continuously based on several patient sleeping positions. With such a system, higher pressure would be supplied to the patient by the pressure source the closer a person's head is to a completely supine position with the patient's nose lying in a vertical plane. Slightly lower pressure could be supplied, for example, if a person's head was 20° off from the supine position and other positions further away from the supine position. The lowest gas pressure would usually be when the patient's head is in a lateral position 90° or more from the supine position.

The patient's head positions are described herein primarily in terms of the supine position, a lateral position and positions between these two positions about a longitudinal axis passing through the patient's head. The head position sensor may also sense when the patient's head is tilted toward or away from the patient's chest, or rotated further than a lateral position 90° away from the supine position. A patient whose head is tilted far forward during sleep (i.e. the chin is close to the chest), may experience an even higher frequency of airway blockages than when in a supine position and may need a higher gas pressure to maintain an open airway passage than when in a supine position.

The PAP system which modulates its output pressure based on a patient's head position while sleeping could also be used to determine whether a given patient's sleep apnea event frequency and severity are affected by sleeping position, and PAP system output could be modulated accordingly. For example, the PAP system pressure may be lowered from about 11 cm (of water) to about 9 cm as the patient moved from a supine to a lateral sleeping position. The system could also further modulate pressure output based upon whether the number of airway blockages increased or decreased (e.g. as measured by pressure sensors in the PAP mask or within the gaseous flow from the compressor to the PAP mask) and the corresponding patient position.

The controller of the PAP system may be used to provide different pressure source output pressures within the pressure envelope at different points in the respiratory cycle at any given patient head positions. For example, higher pressure source output pressures may be provided during inhalation and lower pressure source output pressures during exhalation to maintain the critical pressure within the patient's airway passage.

The features of this invention would allow a PAP system to provide different suitable gas pressures depending on the head position of the patient. This would improve patient comfort while providing the critical pressure at different positions to maintain an open airway. Additionally, since patients prefer lower PAP pressures, such a system might also cause patients to prefer to sleep in positions (such as a lateral position) that cause the system to provide a lower gas pressure to the patient. The lower output pressure would also spur the patient to sleep in a position that leads to fewer airway blockages. The lower output pressure would tend to disturb a person's sleep much less because of comfort of lower pressure and less noise due to the slower operation of the compressor drive motor.

A wearable PAP system embodying features of the invention preferably has one or more housings which insulate the patient's head from heat, sound and vibration from the from the PAP system. For example a pad may be positioned at the bottom of the housing(s) or the bottom of the housing may be spaced from the patient's head to minimize such heat, noise and vibrations. The drive motor for the compressor may have additional vibration and noise dampers to produce a less disturbing operation. Materials such as foams, gels, plastic members, rubber-like members or contained fluids may be used to isolate and/or reduce the noise and vibrations which emanate from the pressure source.

Further, a PAP system embodying features of the invention may be spaced from the top of the patient head and be supported by pod extensions or feet which are secured to the harness assembly. The bottoms of the pod extensions or feet are preferably padded to minimize patient discomfort.

Because a substantial portion of the bottom surface of the housing is spaced away from the patient's head, trapped heat underneath the bottom of the housing is minimized. The open space between the patient's head and the bottom of the housing(s), in addition to providing ventilation also reduces noise and vibration from the system housing to the patient.

Moreover, because a self-contained PAP system embodying features of the present invention does not have a gas delivery tube connecting the patient's face mask to a remote pressure generating unit, there are fewer restrictions on a patient's movement during sleep. There is little or no likelihood of pulling the mask away from its operative position on the patient's face, and there is no remote pressure generating unit which might be pulled off an adjacent night stand.

These and other advantages of the invention will become more apparent from the following detailed description of embodiments of the invention when taken in conjunction with the accompanying exemplary drawings.

DETAILED DESCRIPTION OF EMBODIMENTS OF THE INVENTION

Figure 1:
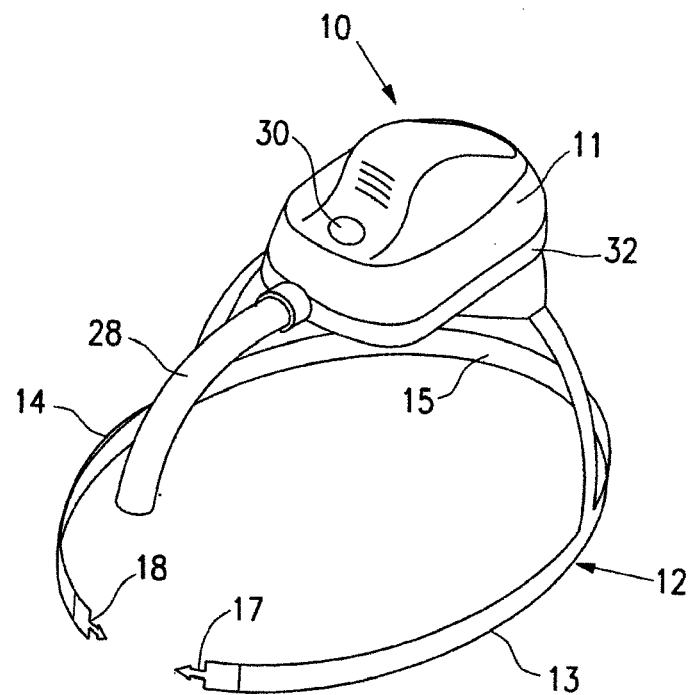
FIG. 1 shows a perspective view of a PAP system embodying features of the invention.
Figure 2:
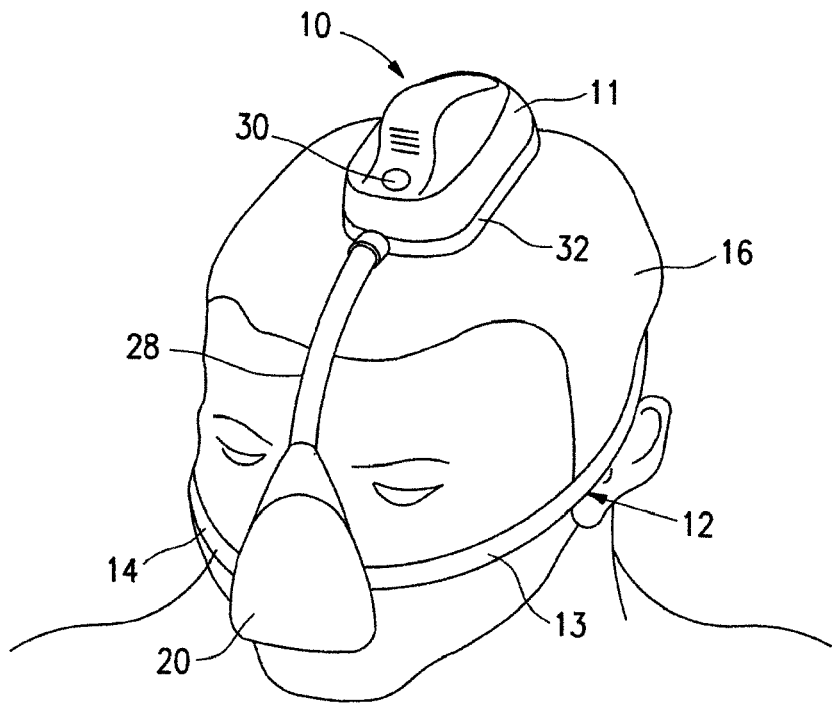
FIG. 2 is a perspective view of a PAP system shown in FIG. 1 with a mask mounted over the patient's nose and the housing mounted on the patient's head.
Figure 3:
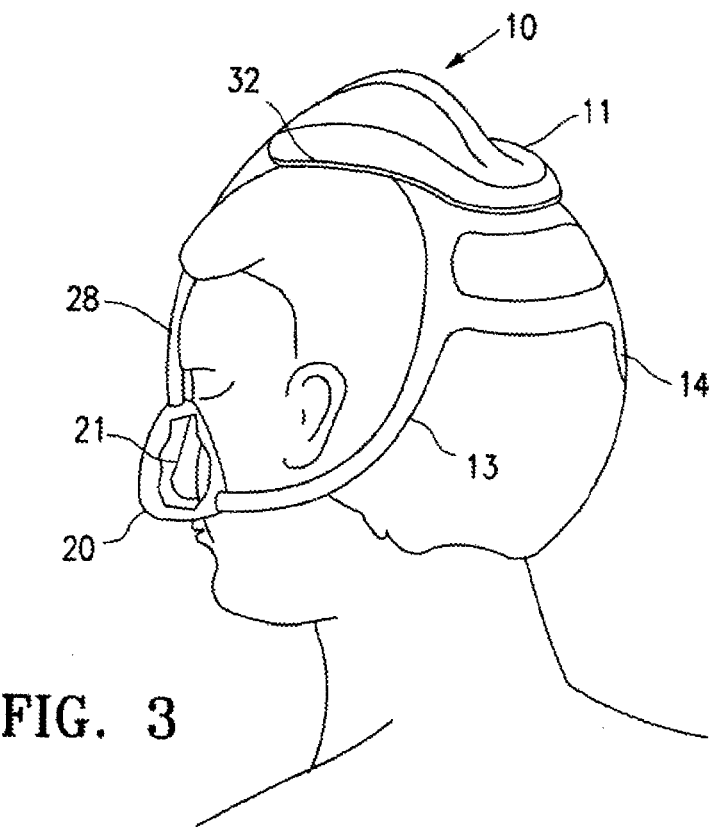
FIG. 3 is a rear view of the PAP system shown in FIG. 2.

FIGS. 1-3 are perspective views of a PAP system 10 embodying features of the invention. As shown, the system 10 basically includes a system housing 11 and a harness assembly 12 secured to the bottom of the housing. The harness assembly 12 has a plurality of straps 13 and 14 and cross strap 15 to secure the housing 11 to a patient's head 16 as shown in FIG. 2. The free ends of straps 13 and 14 have push in type connectors 17 and 18, as shown in FIG. 1, for securing the free ends to mask 20 as shown in FIG. 2. The straps 13-15 hold the mask 20, as shown in FIG. 2, in a sealed engagement with the patient's nose 21.

Figure 4:
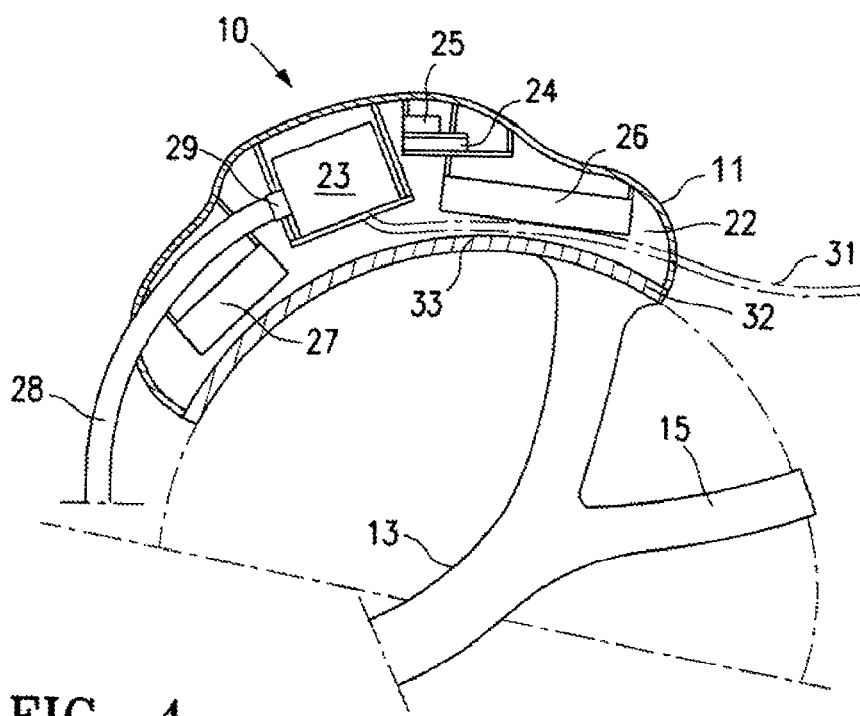
FIG. 4 is a side elevational view of the system shown in FIG. 1 with portions of the system housing removed to illustrate the various components within the system housing.
Figure 5:
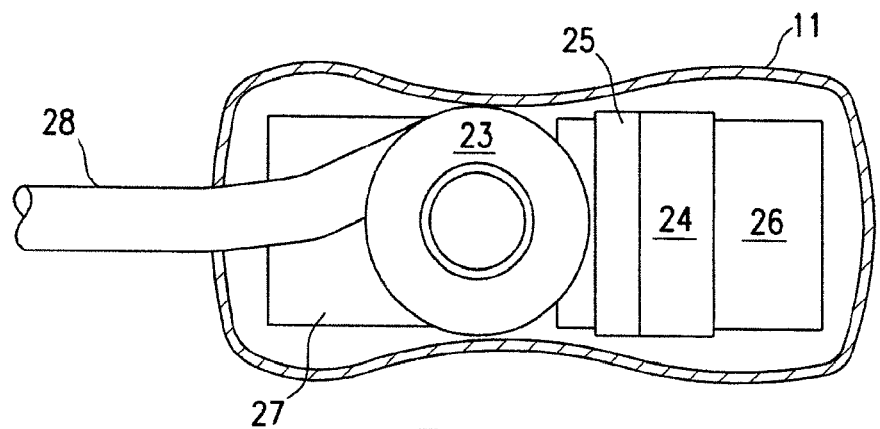
FIG. 5 is a top view of the system with portions of the system housing removed to illustrate the various components within the system housing.

As best shown in FIGS. 4 and 5, the interior 22 of system housing 11 contains a compressor 23, a controller 24, a position sensor 25 and batteries 26 and 27 to supply electrical power to the compressor 23. A gas delivery tube 28 is secured to the discharge 29 of the compressor 23 and extends to the mask 20 for the delivery of a breathable gas to the patient's nose 21 as shown in FIG. 2. A system activation/calibration button 30 may be provided on the front of the housing 11. An electrical power chord 31 (shown in phantom) may be provided for powering the compressor 23 directly from a separate electrical source such as an electrical outlet or battery pack (not shown) or for recharging one or more of batteries 26 and 27. A vibration and sound deadening layer 32 may be provided on the bottom 33 of the system housing 11 and between the compressor 23 and supporting structure (not shown) therefore.

Figure 6:
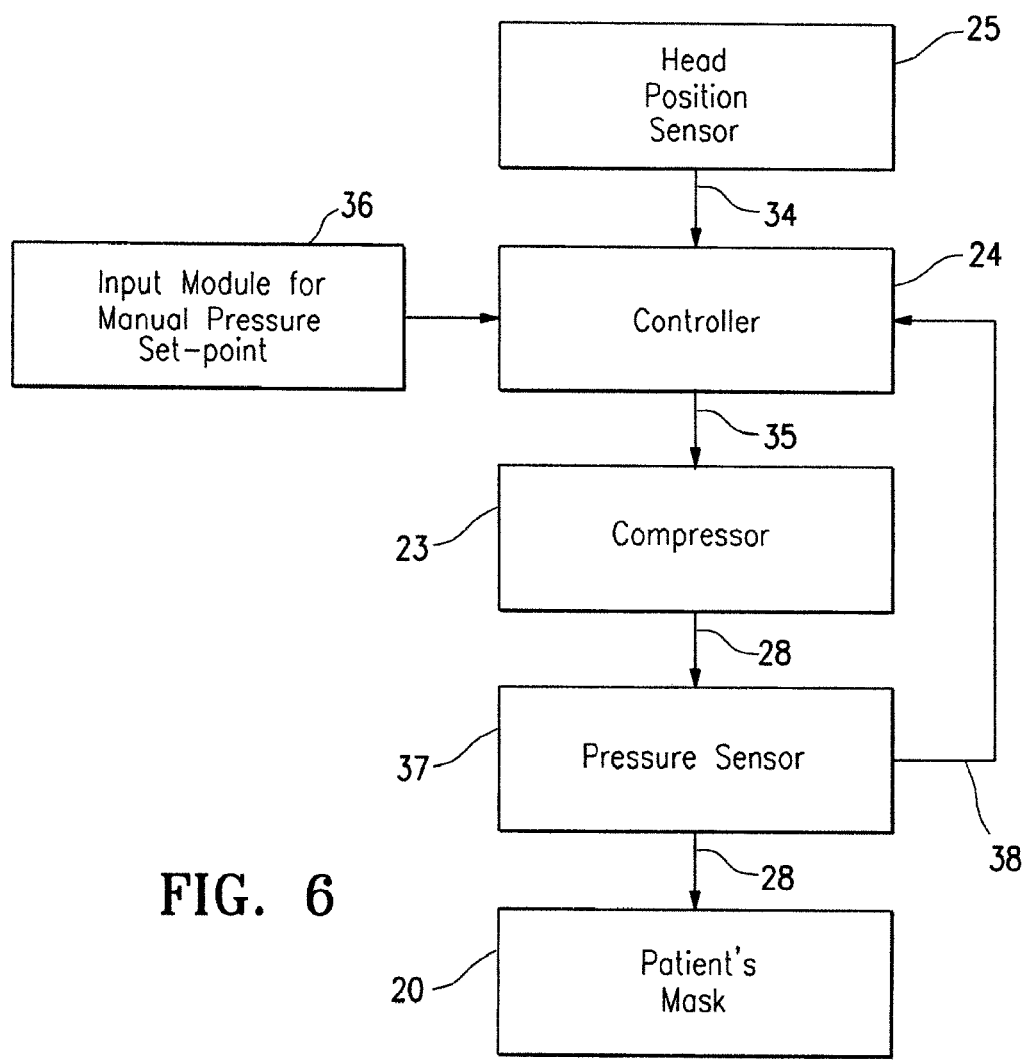
FIG. 6 is a block diagram illustrating the system shown in FIG. 1.

FIG. 6 is a block diagram of the system 10 illustrating the interconnection of the various components of the system. A position signal 34 from the head position sensor 25 is transmitted to the controller 24 which in turn generates a control signal 35 for the compressor 23 based upon the received head position signal 34. The controller 24 may have an input module 36 that allows for the manual input of compressor output pressure set point(s) that provides one or more suitable compressor output pressures for the compressor for one or more received head position signals 34. The gas delivery tube 28 which delivers pressurized gas from the compressor 23 to the mask 20 may have a pressure sensor 37 which generates a pressure signal 38 that is fed back to the controller 24 to ensure that the desired gas pressure for the sensed patient position is delivered to the patient. The pressure sensor 37 may be alternatively located in the patient's mask 20 or the compressor discharge 29.

Figure 7:
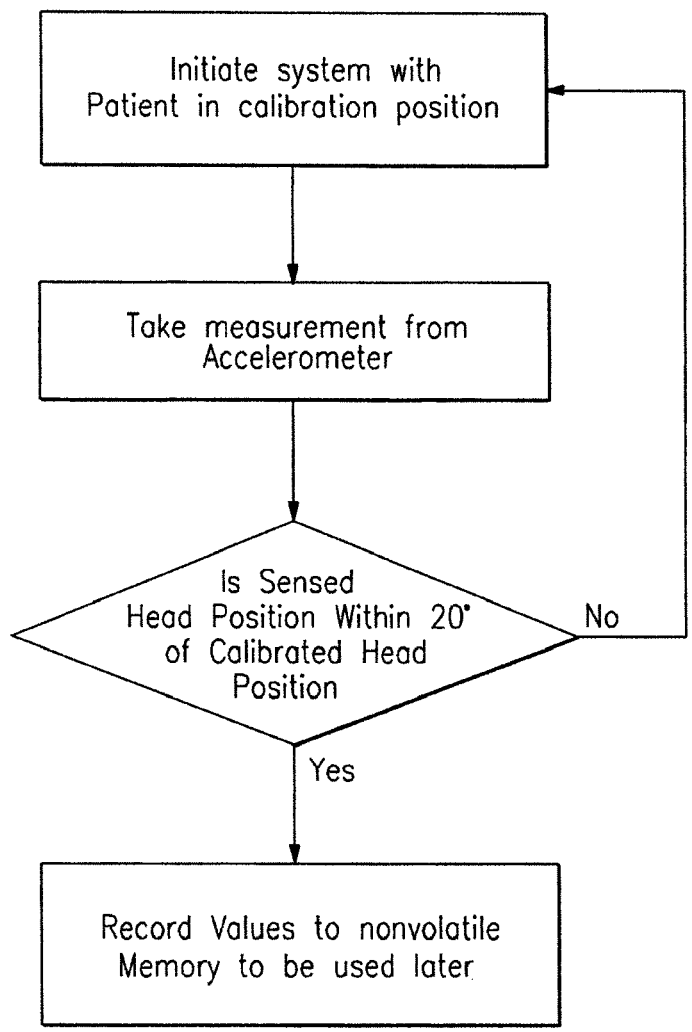
FIG. 7 is a flow diagram illustrating position calibration of the system processing.

FIG. 7 is a flow diagram illustrating the calibration of the head position sensor 25. With the PAP system 10 mounted onto the patient's head, the patient reclines into a calibration position, such as the supine position, and pushes the activation button 30 on the front of the housing 11. The preferred head position for calibrating the sensor 25 is the supine position with the patient's nose is orthogonal to the sleeping plane 40. The system takes a measurement from the head position sensor 25, an accelerometer, and compares this measurement to the Gravitational constant (G). Once the measurement is within 10% of G, the value is recorded to a nonvolatile memory in the controller 24. The system 10 may be calibrated by the patient or by a health professional.

Figure 8:
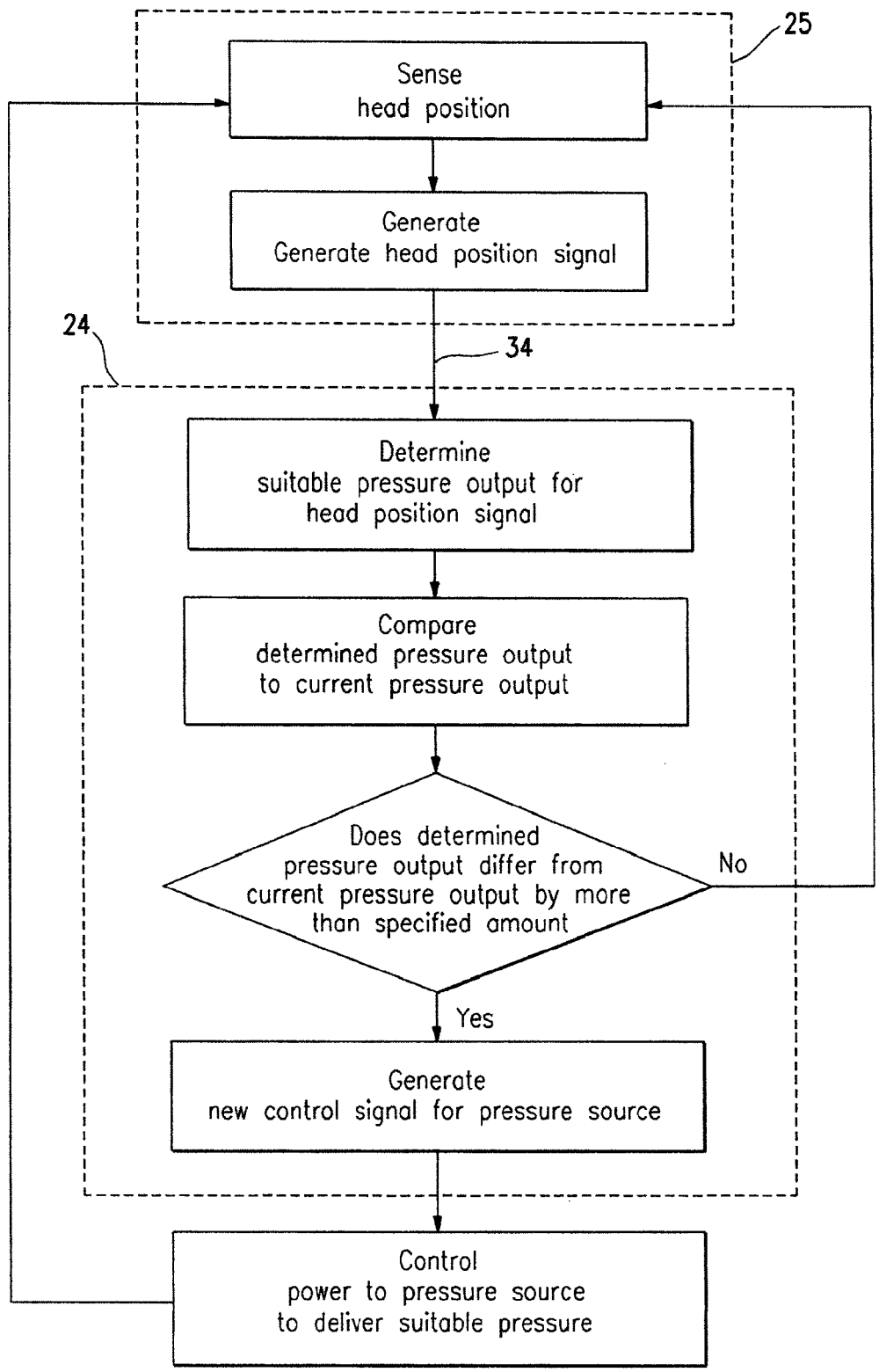
FIG. 8 is a flow diagram illustrating processing for a PAP system embodying features of the invention.

FIG. 8 is a flow diagram illustrating an operation of the calibrated PAP system 10 embodying features of the invention. The calibrated head position sensor 25 senses the patient's head position and generates a head position signal 34 representing then sensed head position. This signal 34 is transmitted (by a wire or wirelessly) to controller 24, compares the received head position signal 34 with a stored relationship between head position signal and compressor output pressure and determines a suitable compressor output pressure for the sensed head position. The controller 24 compares this determined pressure output to the current pressure source output pressure, and, if the determined pressure output differs from the current pressure output by more than a specified amount, then the controller will generate a new control signal for the pressure source or compressor. This new control signal will control the pressure source to deliver a suitable output pressure that is delivered to the patient or user through a mask 20 so as to maintain a critical pressure within the patient's airway passage. If the determined pressure output does not differ from the current pressure output of the pressure source by more than a specified amount, the control signal will not be changed. The system 10 will continue to sense the head position of the patient and restart the loop.

In another embodiment, the input module 36 may be used by a health professional to input a set-point for a suitable compressor output pressure for the calibrated sensor head position that has been determined by the patient's sleep test. The controller 24 may continuously or periodically compare the sensed head position signal 34 from the position sensor 25 with the calibrated head position signal. If the comparison indicates that the patient's sensed head position deviates from the calibrated head position less than a certain amount, e.g. 20°, then the system will loop (providing the same control signal 34 to the compressor to provide a suitable compressor output pressure) until the controller detects a head position signal which represents a sensed head position that deviates more than the certain amount. When the controller 24 determines that the sensed head position deviates more that the certain amount, such as the lateral position, the controller compares the head position signal 34 with a stored relationship between head position signal and suitable compressor output pressure to determine the suitable compressor output pressure for the new sensed head position such as the lateral head position where the patient's nose lies in a plane 41 parallel to the sleeping plane 40 when the patient's head 16 is resting on pillow 42. The controller 24 then generates a new control signal 35 for the compressor to enable the compressor to provide the suitable output pressure for the sensed new lateral head position. The system 10 will loop providing the same output pressure until a new head position signal 34 indicates that the patient's head is in a new position which is more than 20° away from the lateral position.

Figure 9:
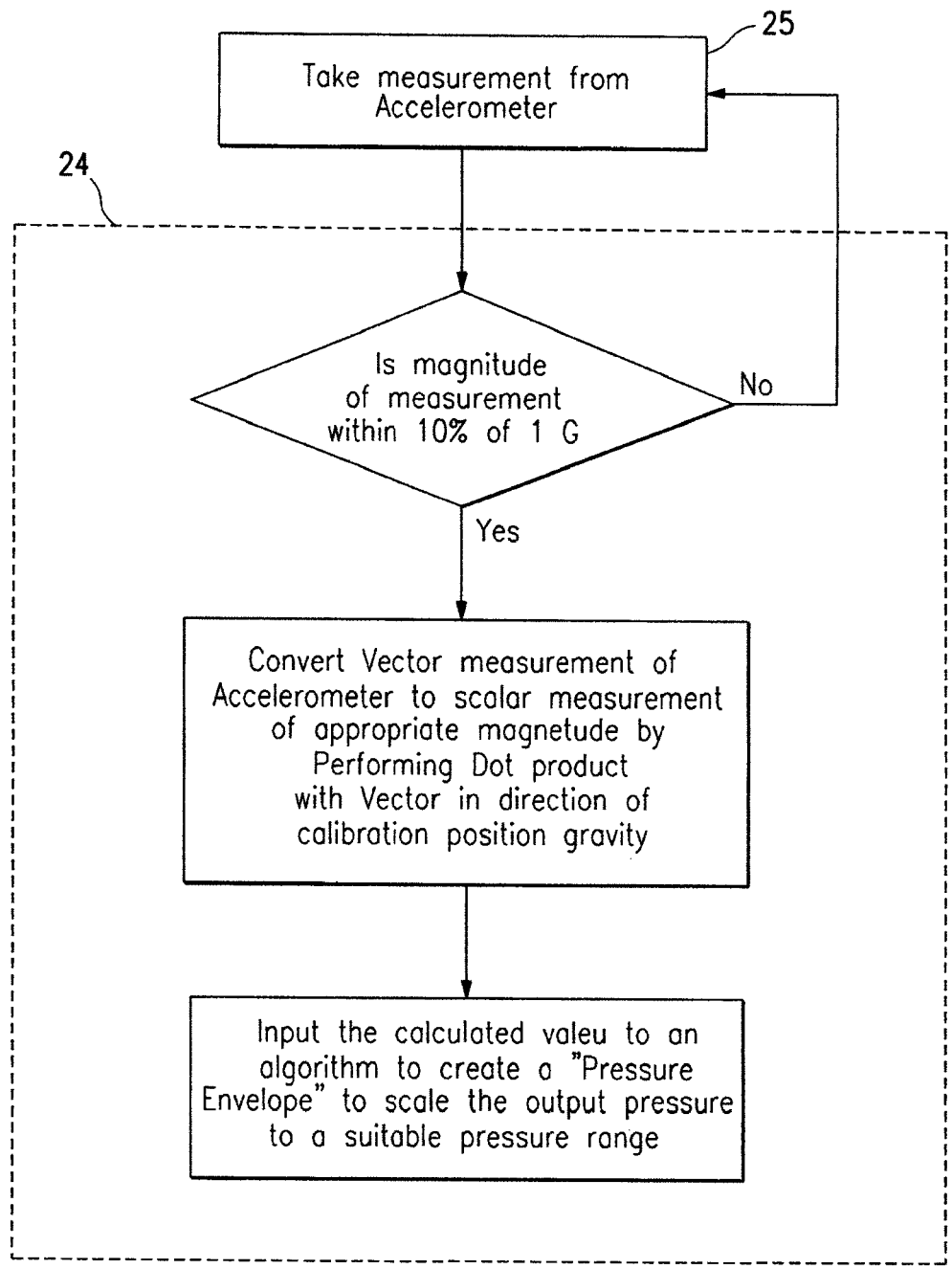
FIG. 9 is a flow diagram illustrating system processing using scalar measurement.

A flow chart is shown in FIG. 9 illustrating a way to scale the pressure calculation as the head is moved from the calibrated position. The position sensor 25, an accelerometer, takes a measurement which is compared with gravity to determine if the accelerometer is stabilized. If the measurement is within 10% of G, the vector measurement of the accelerometer is converted to a scalar measurement by performing a Dot product, using the vector in the direction of the calibration position gravity. Next, a minimum pressure is added to the scalar reading and then a pressure envelop is created to control the output pressure of the pressure source.

Figure 10:
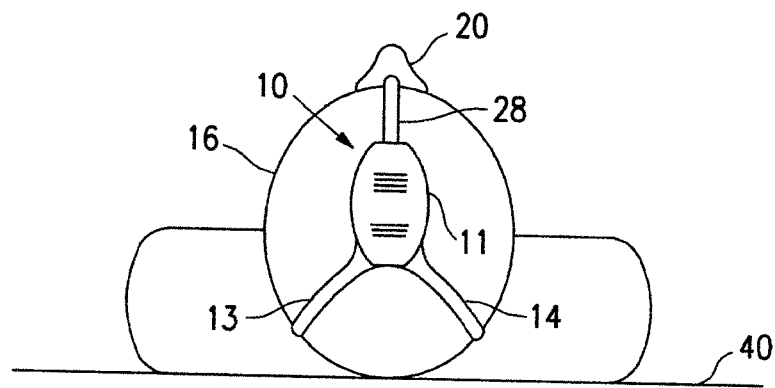
FIG. 10 is a top view of the PAP system shown in FIG. 2 with the patient's head in the supine position and the patient's nose pointed directly up, orthogonal to the sleeping plane.

FIG. 10 shows the top view of a patient wearing a PAP system 10 embodying features of the invention while lying in the supine position with the head 16 and nose pointed directly up, orthogonal to the sleeping plane 40. This is the preferred calibration position. A patient sleeping in the supine position will generally require a pressure that is higher than what is required in more lateral sleeping positions.

Figure 11:
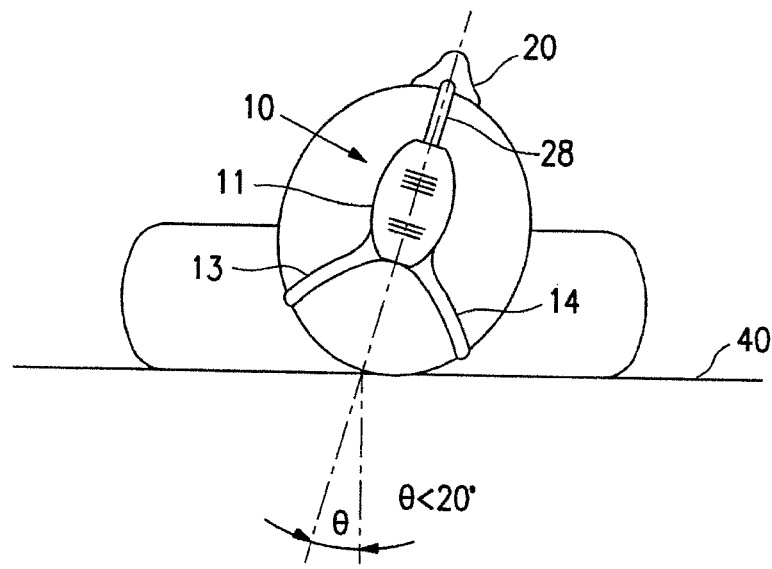
FIG. 11 is a top view of the PAP system with the patient's head less than 20° from the supine position.

FIG. 11 shows a top view of a patient wearing a PAP system 10 embodying features of the invention while lying with his or her torso in the supine position and the head 16 rotated slightly laterally. In this figure, angle theta represents the deviation of the head from a true supine position, here shown to be less than 20°.

Figure 12:
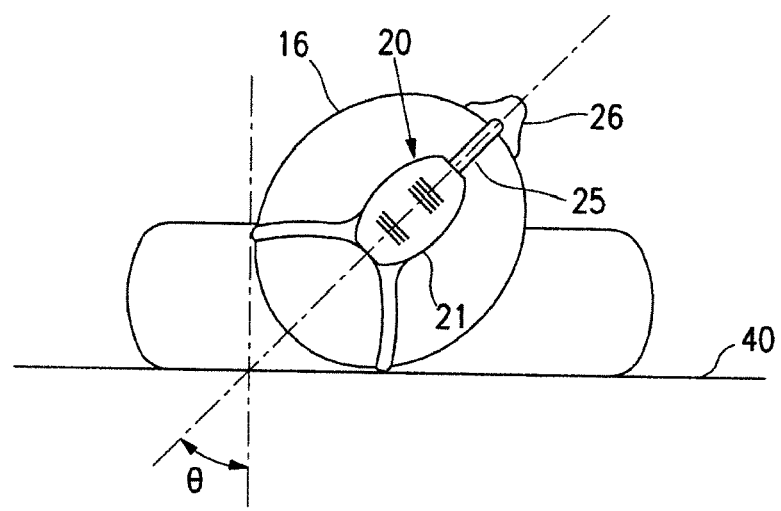
FIG. 12 is a top view of the PAP system with the patient's head about 30°-60° from the supine position.

FIG. 12 shows the top view of a patient wearing a PAP system 10 embodying features of the invention while lying with the patient's torso in the supine position and the patient's head 16 rotated more laterally. In this Figure, angle theta represents the deviation of the head from a true supine position, here shown to be between 30° and 60°.

Figure 13:
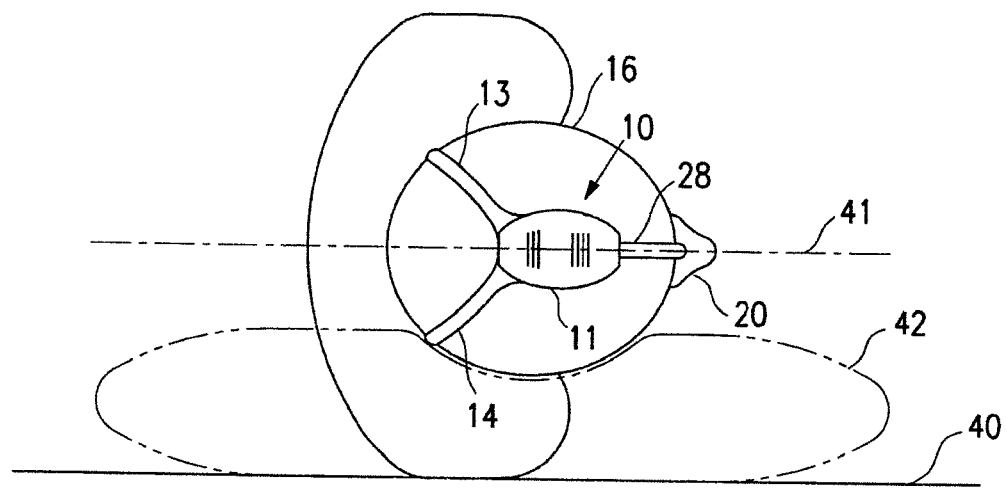
FIG. 13 is a top view of the PAP system with the patient's head in the lateral position 90° from the supine position.

FIG. 13 shows a top view of a patient wearing a PAP system 10 embodying features of the invention while lying with the patient's torso in the lateral position and the head 16 of the patient in a neutral lateral position inn pillow 42 with the nose pointed in a plane 41 parallel to the sleeping plane 40.

Figure 14:
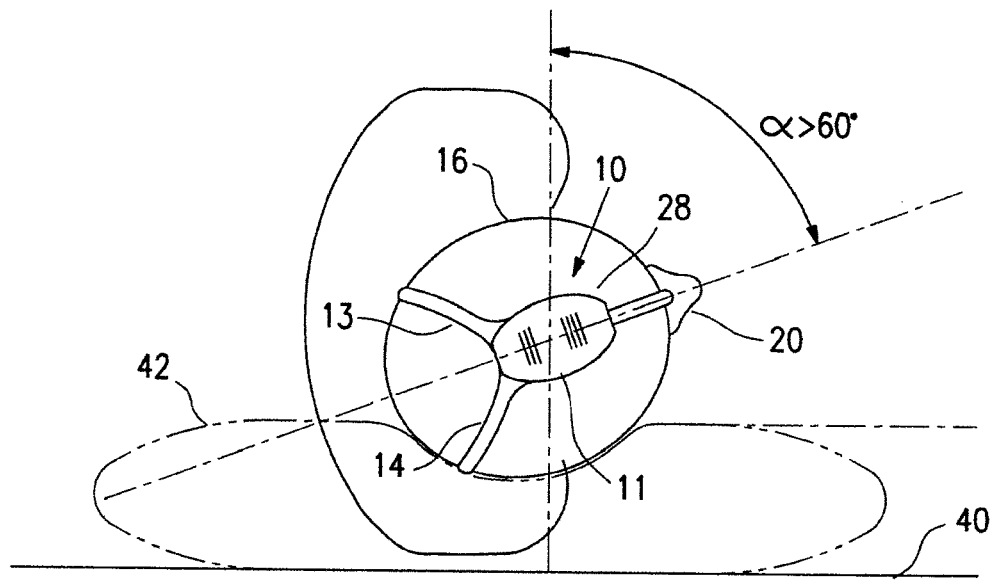
FIG. 14 is a top view of the PAP system with the patient's torso in a lateral position and the patient's head in a position greater than 60° and less than 90° from the supine position.

FIG. 14 shows a top view of a patient wearing a PAP system 10 embodying features of the invention while lying with the torso in the lateral position and the head 16 rotated toward the supine direction relative to the lateral sleeping position which is parallel to the sleeping plane 40. Angle alpha represents the rotation of the patient's head from true supine position, here shown to be less than 90°.

Figure 15:
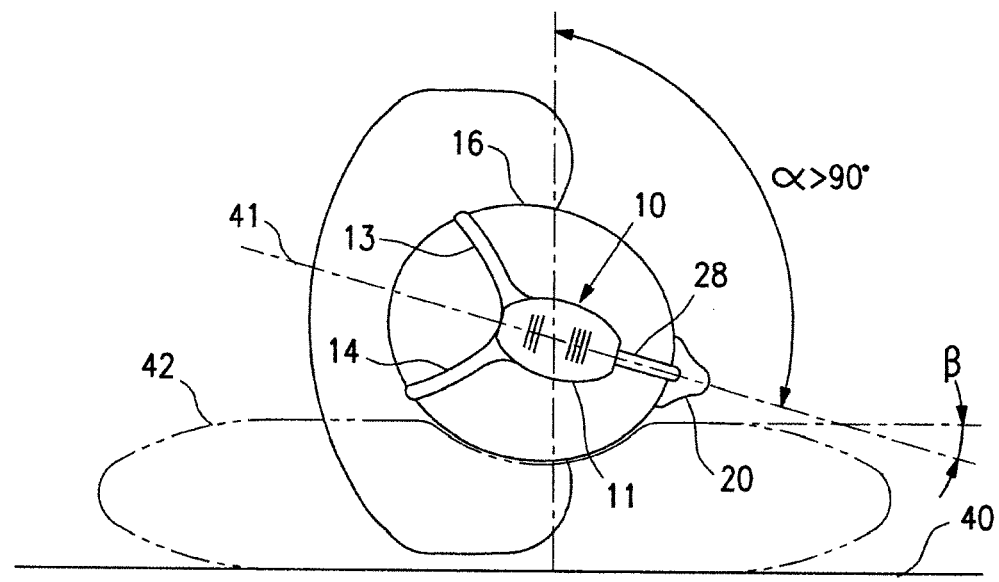
FIG. 15 is a top view of the PAP system with the patient's torso in a lateral position and the patient's head in a position greater than 90° from the supine position.
Figure 16:
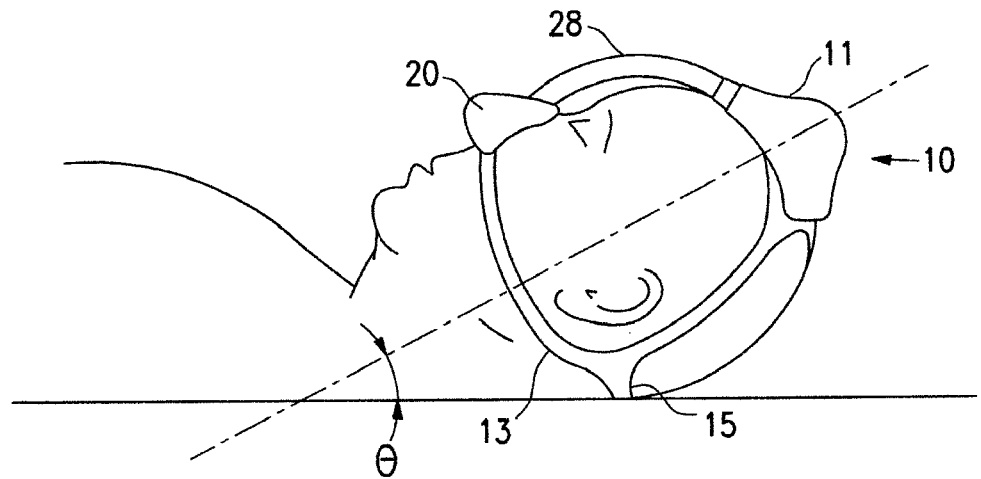
FIG. 16 shows a side view of a user with the head tilted down, bringing the chin closer to the user's chest.

FIG. 15 shows the top view of a patient wearing a PAP system 10 embodying features of the invention while lying with the patient's torso in a lateral position and the patient's head 16 rotated beyond 90° from the supine position FIG. 16 shows a side view of a patient wearing a PAP system 10 embodying features of the invention while lying with the patient's torso and head 16 in the supine position with the head tilted forward such that the patient's chin is closer to the patient's chest.

Figure 17:
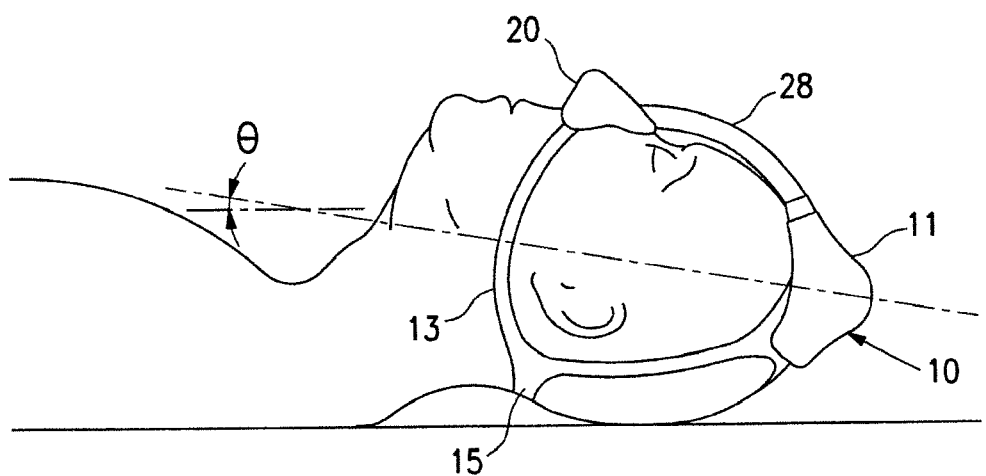
FIG. 17 shows a side view of a user with the head tilted up, moving the chin further away from the user's chest.
Figure 18:
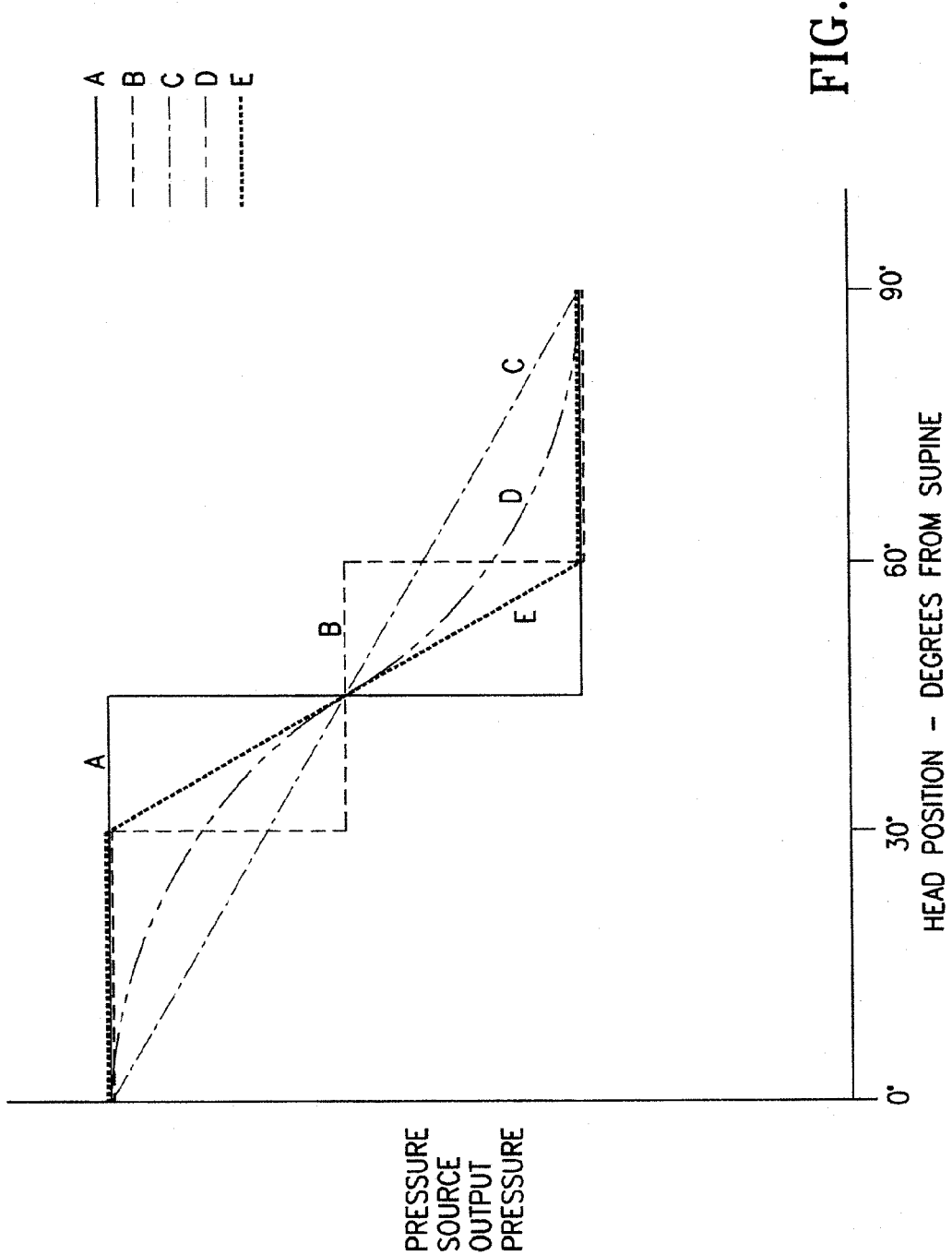
FIG. 18 illustrates how different algorithms can relate head position input signals (i.e. representing degrees from a supine position) and suitable pressure source output pressures.

FIG. 17 shows a side view of a patient wearing a PAP system 10 embodying features of the invention while lying with the patient's torso and head 16 in the supine position with the head tilted backward such that the patient's chin is further from the patient's chest.

The controller may be programmed to provide a suitable compressor output pressure for positions such as when the patient's head is rotated more than 90° from the supine position as shown in FIG. 15 and for position such as when the patient's head is tilted forward or backward as shown in FIGS. 16 and 17. The stored relationship between the sensed head position signal 34 and suitable compressor output pressure may be a list of sensed head position signals with corresponding suitable compressor output pressures in a readable library in the controller 24. Alternatively, the stored relationship may be an algorithm which defines a curve of head position verses compressor output pressure.

The relationship between the sensed position of the patient's head and the pressure output of the pressure source can take several forms, as depicted in the graph shown in FIG.

18. Line A depicts a step function in which, at some point between supine position and a position 90° from the supine position, the pressure output drops. Such a step function could also have multiple steps between the supine position and 90° from the supine position, as depicted in line B.

Alternatively, the relationship between head position and output pressure may follow an inclined straight line, as depicted by line C Another possibility is shown in line D which depicts a relationship in which there is a continuous pressure drop moving from a supine position to 90° from supine, but the rate of pressure drop is greatest between 30° and 60° from the supine position. Yet another relationship is shown in line E wherein there is an inclined linear portion between the supine pressure and lateral pressure between 30° and 60°.

While not shown, the pressure could continue to drop at positions greater than 90° from the supine position. Additionally, the relationship between pressure and sensed head position may have a more elaborate, advanced curve shape to provide more appropriate pressures at each position. Other relationships may be employed.

Figure 19:
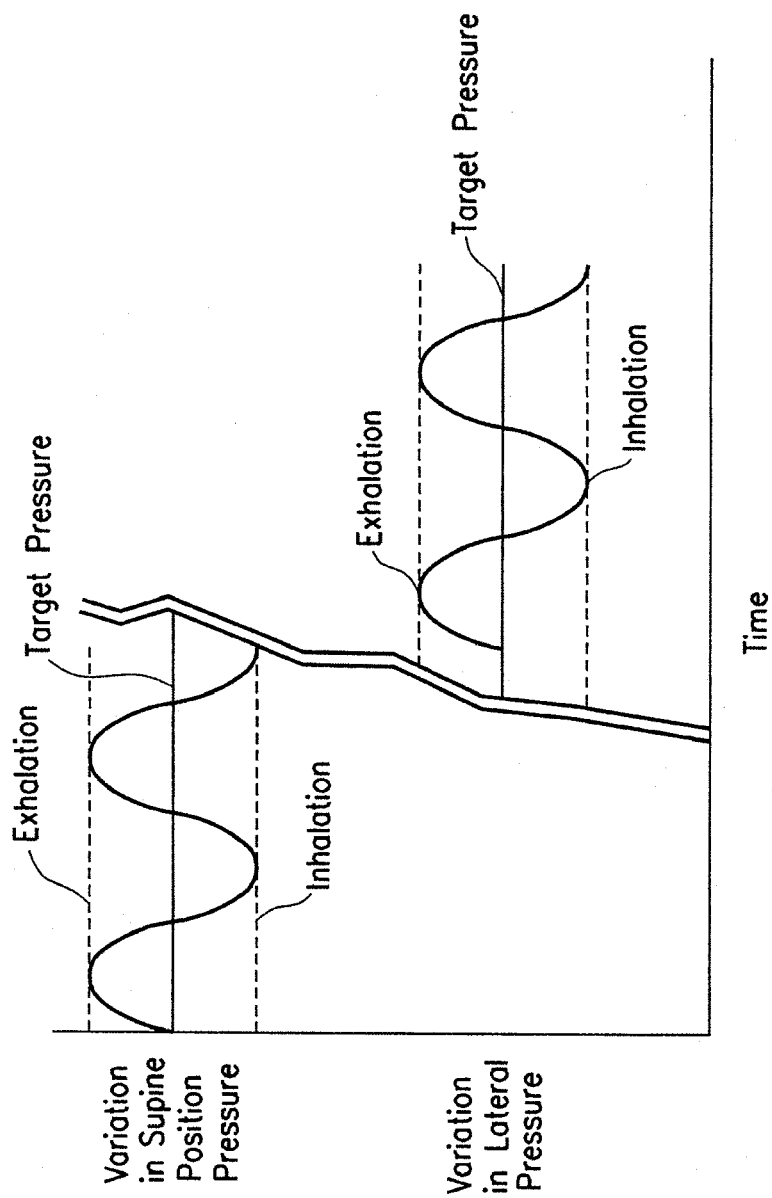
FIG. 19 is a graph schematically illustrating output pressure variations within a pressure envelope for a supine and a lateral head positions.

FIG. 19 graphically illustrates a respiratory cycle through two different head positions supine and lateral. In the supine position, the delivered pressure is higher and the respiratory cycle causes the pressure to fluctuate within a range about the clinical target pressure between inhalation and exhalation. In the lateral position, the delivered pressure is lower and fluctuates between inhalation and exhalation similar to the fluctuations in the supine position.

Figure 20:
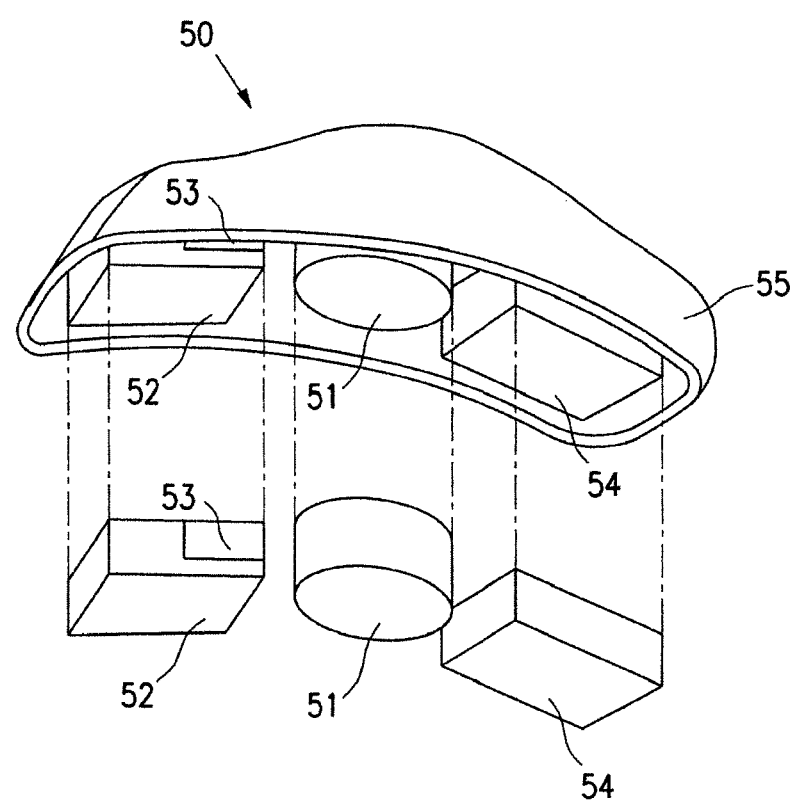
FIG. 20 is an exploded perspective view of a housing for a PAP system showing how the components are fit into the interior of the housing.
Figure 21:
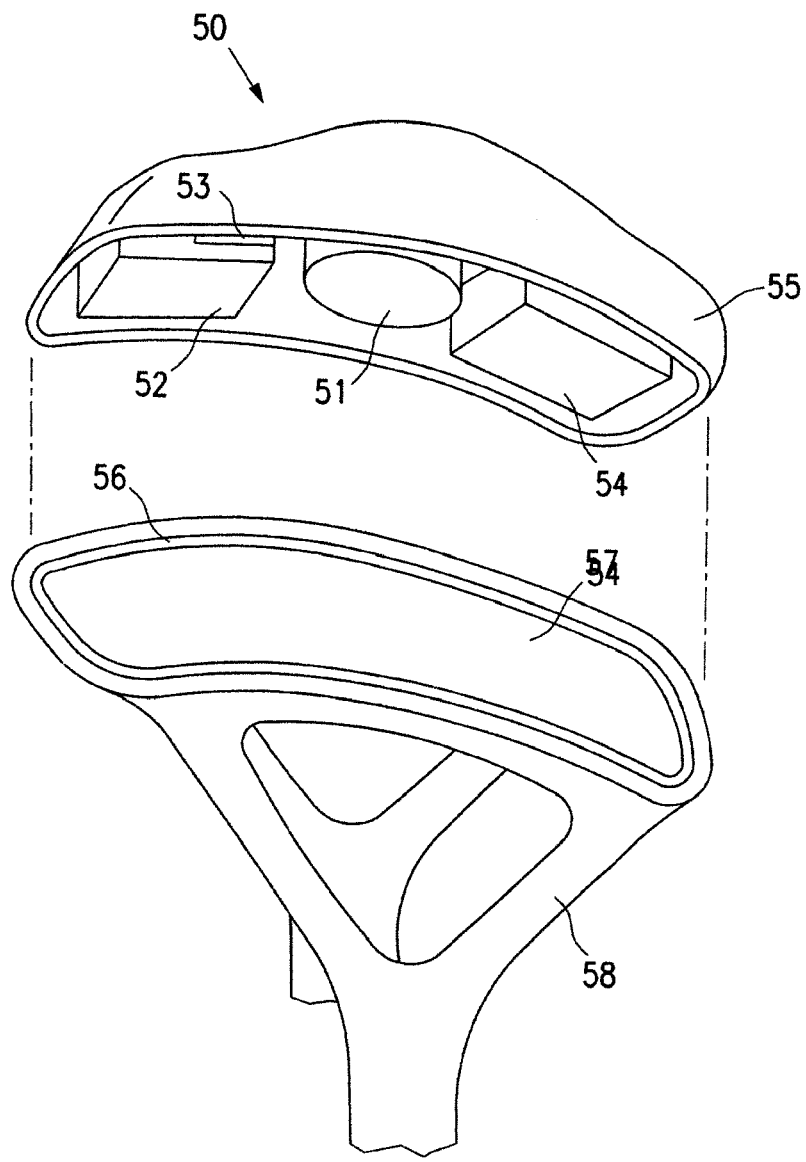
FIG. 21 illustrates how the housing shown in FIG. 19 interfaces with a replaceable strap structure or harness assembly for securing the PAP system to the head of a patient or user. The shaded contact interface securely attaches the PAP system to the strap structure.

An alternative PAP system 50 embodying features of the invention is shown in FIG. 20 in an exploded view. In this embodiment, the compressor 51, controller 52, position sensor 53 and battery 54 are secured to the top inner lining of the housing 55. The lower margins of housing 55 are secured to the shaded areas 56 of base 57 which is secured to the replaceable harness assembly 58 as shown in FIG. 21. In this manner the housing 55 along with the secured components 51-54 could be reusable, whereas the harness assembly 57 and 58 which has direct contact with the patient can be easily replaced as needed. The shaded contact areas 56 of the base 57 may be recessed so as to provide a better fit for the lower margins of the housing 55.

Figure 22:
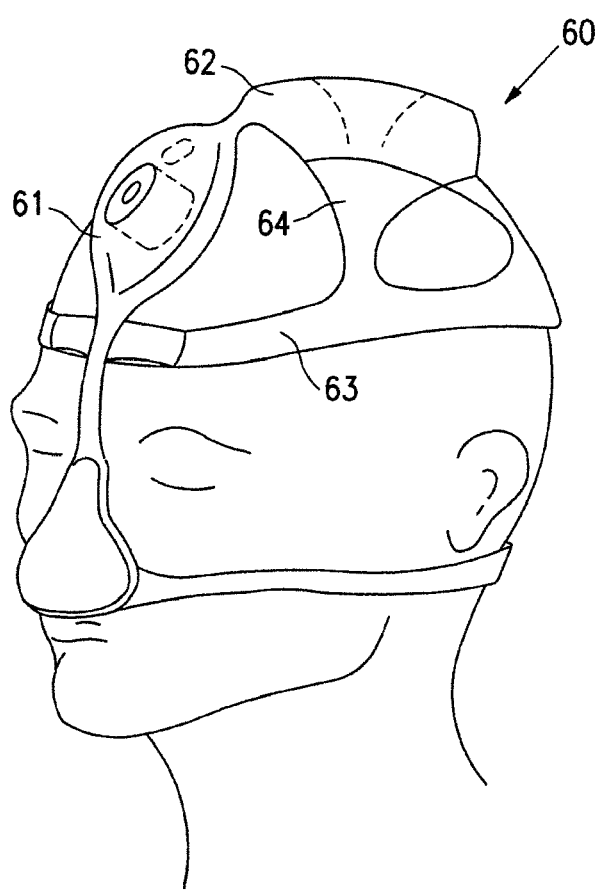
FIG. 22 is a perspective view which depicts a PAP system which has multiple housings to contain the various components of the system.

Another alternative embodiment is shown in FIG. 22 wherein a PAP system 60 embodying features of the invention has multiple housings, housing 61 which holds the compressor and housing 62 which holds the controller and battery. Housings 61 and 62 are secured to the harness assembly 63 which holds the system 60 against the patient's head. The position sensor is secured to the interior of one of the housings, preferably to the controller that is secured to the housing 62. With this particular configuration of the PAP system 60, the weight of the PAP system can be more evenly distributed over the top of the patient's head. Moreover, a smaller area of the patient's head is covered with the housing which improves the comfort and heat regulation and reduces potential irritation of the patient's scalp. Additionally, the harness assembly 63 may have a flexible base 64 and the multiple housings 61 and 62 secured to the flexible base can better conform to the shape of the patient's head and facilitate easier replacement of the various components of the system. Other advantages are apparent.

Figure 23:
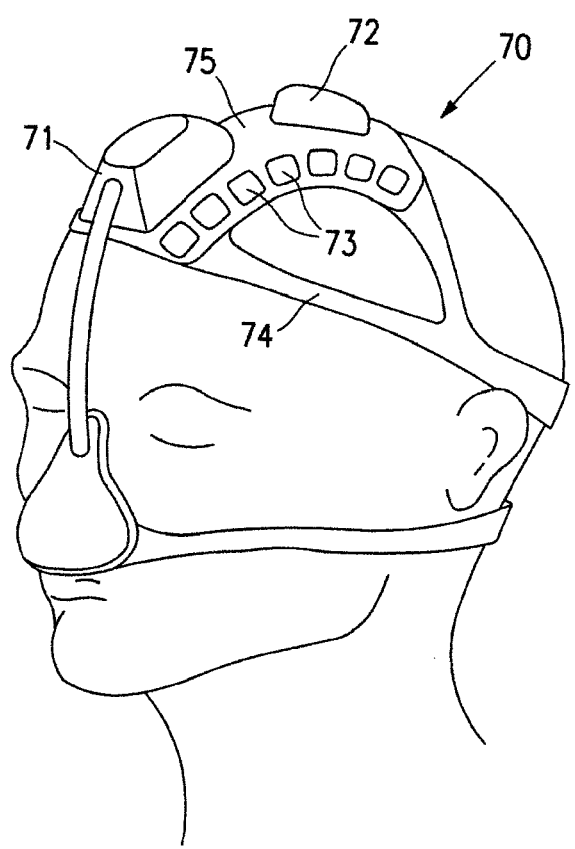
FIG. 23 is a perspective view showing a PAP system with multiple housings that are interconnected by a fabric or mesh that is integral with the harness assembly.

FIG. 23 illustrates yet another alternative PAP system 70 having multiple housings which contain system components. In PAP system 70, housing 71 contains the pressure source and motor drive (not shown) and housing 72 contains the controller (not shown). The electrical power source is a plurality of battery cells 73 which are secured to the harness assembly 74, preferably to a flexible base 75 which is part of the harness assembly. The harness assembly 74 secures the multiple housings 71 and 72 and battery cells 73 to the patient's head. Conductor wire(s) (not shown) interconnect the battery cells 73 and the motor drive for the compressor and the controller and the motor drive for the compressor.

Figure 24:
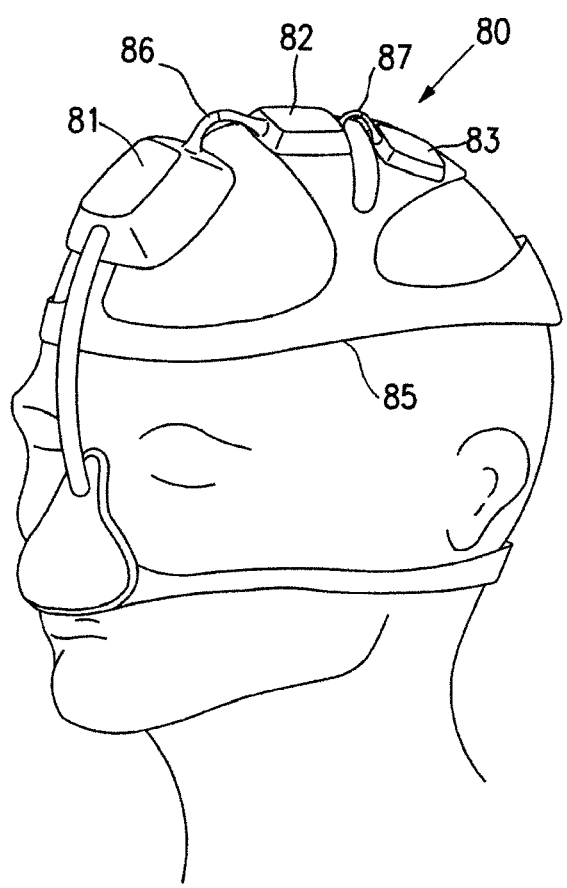
FIG. 24 is a perspective view that illustrates a PAP system having multiple housings interconnected by hinged, semi-rigid elements.

FIG. 24 illustrates yet another alternative PAP system 80 having multiple housings which contain system components. In PAP system 80, housing 81 contains the pressure source and motor drive (not shown) and housing 82 contains the controller (not shown). Housing 83 contains the electrical power source such as one or more batteries (not shown). The plurality of housings 81-83 are secured to a harness assembly 85. The individual housings 81-83 are interconnected by flexible connections or joints 86 and 87. The harness assembly 85 secures the multiple housings 81, 82 and 83 to the patient's head. Conductor wire(s) (not shown) interconnect the electrical power source and the motor drive for the compressor and conductor wires (not shown) connect the controller and the motor drive for the pressure source.

While particular forms of the invention have been illustrated and described herein, it will be apparent that various modifications and improvements can be made to the invention. For example, while the description herein has focused on PAP systems, the system may be utilized in a variety of breathing systems. Additionally, the PAP systems are primarily described herein as self-contained breathing systems. However, many of the advantageous features described herein may be applicable to breathing systems with remote control and/or pressure sources and wherein the head position sensor is secured to the top of the patient's head. To the extent not otherwise described herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents, patent applications and publications referred to above are hereby incorporated by reference in their entirety.

What is claimed is:

1. A method for providing pressurized air to an airway of a patient, the method comprising:
   delivering pressurized air from a pressure source to the patient's airway;
   sensing the patient's head position with a sensor; and
   adjusting, using a controller, pressure of the pressurized air so that pressure delivered is at a maximum when the patient's head position is a supine head position, there is a pressure drop of the pressurized air delivered when the patient's head is at a position between the supine head position and a position 90° from the supine head position, and there is a maximum rate of pressure drop of the pressurized air delivered when the patient's head is between 30° and 60° from the supine head position.

2. The method of claim 1 wherein the adjusting step comprises adjusting pressure in multiple pressure drop steps between the supine head position and the position 90° from the supine head position.

3. The method of claim 1 wherein the rate of pressure drop between 30° and 60° from the supine head position is constant.

4. The method of claim 1 wherein the adjusting step comprises adjusting pressure in a plurality of pressure steps between the supine head position and 90° from the supine head position.

5. The method of claim 1 wherein the delivering step comprises delivering the pressurized air to the patient's airway through a mask attached to the patient.

6. The method of claim 1 further comprising attaching a head position sensor to the patient's head.

7. A positive airway pressure system for delivering pressurized air to an airway of a patient, the system comprising:

a pressure source configured to provide the pressurized air;

a mask configured to deliver the pressurized air to the patient's airway;

a head position sensor configured to generate an output signal indicative of a position of the patient's head; and a controller configured to receive the head position sensor output signal and to adjust pressure of the pressurized air so that the pressure is at a maximum when the patient's head position is a supine head position, there is a pressure drop of the pressurized air delivered when the patient's head is at a position between the supine head position and a position 90° from the supine head position, and there is a maximum rate of pressure drop of the pressurized air delivered when the patient's head is between 30° and 60° from the supine head position.

8. The system of claim 7 wherein the head position sensor is configured to be attached to the patient's head.

* * * * *